United States Patent
Stoianovici et al.

(10) Patent No.: US 6,400,979 B1
(45) Date of Patent: *Jun. 4, 2002

(54) FRICTION TRANSMISSION WITH AXIAL LOADING AND A RADIOLUCENT SURGICAL NEEDLE DRIVER

(75) Inventors: Dan Stoianovici, Baltimore; Louis R. Kavoussi, Lutherville; Louis L. Whitcomb, Baltimore; Russell H. Taylor, Severna Park; Jeffrey A. Cadeddu, Baltimore; Roger D. Demaree, Sykesville; Stephen A. Basile, Gaithersburg, all of MD (US)

(73) Assignee: Johns Hopkins University, Baltimore, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/026,669

(22) Filed: Feb. 20, 1998

Related U.S. Application Data

(60) Provisional application No. 60/038,115, filed on Feb. 20, 1997.

(51) Int. Cl.$^7$ ................................................ A61B 5/00
(52) U.S. Cl. ........................ 600/427; 600/429; 600/567
(58) Field of Search ............................... 600/411, 417, 600/427, 429, 562, 566, 567, 568

(56) References Cited

U.S. PATENT DOCUMENTS

| | | | | |
|---|---|---|---|---|
| 5,415,169 A | * | 5/1995 | Siczek et al. | ................ 600/568 |
| 5,571,147 A | * | 11/1996 | Sluijter et al. | ................ 607/99 |

* cited by examiner

Primary Examiner—Ruth S. Smith
(74) Attorney, Agent, or Firm—Pillsbury Winthrop LLP

(57) ABSTRACT

A method for performing radiological-image-guided percutaneous surgery with a system which includes a radiological image generating device for generating an image of a target anatomy of a patient, and a needle insertion mechanism disposed adjacent the image generating device and having a needle adapted to be inserted into the patient. The method includes the steps of: determining a needle trajectory of the needle by positioning the image generating device for aligning, in the image generated by the image generating device, a desired skin insertion site of the patient with a target region of the target anatomy; locking the needle in a direction of the needle trajectory; and repositioning the image generating device to obtain a lateral view of the needle trajectory for viewing an insertion depth and path of the needle during its insertion into the patient. Moreover, a motion transmission mechanism includes an output shaft and an output shaft driver which has two rotational components having respective contact faces between which the output shaft is pressed for frictional engagement therewith. The frictional engagement creates a force between the output shaft and the rotational components which is parallel to the rotational axis of the rotational components for allowing the rotational components to impart a translational motion to the output shaft by virtue of their rotational motion.

4 Claims, 6 Drawing Sheets

FRICTION TRANSMISSION WITH AXIAL LOADING AND A RADIOLUCENT SURGICAL NEEDLE DRIVER

This application claims the benefit of priority based upon U.S. Provisional Application No. 60/038,115, filed on Feb. 20, 1997, the entire disclosure of which is hereby incorporated by reference.

BACKGROUND OF THE INVENTION

1. Field of the Invention

The present invention pertains to a method and system for radiological image guidance in percutaneous surgery. The invention further pertains to a friction transmission mechanism with axial loading.

2. Description of the Related Art

As an alternative to traditional open surgery, percutaneous surgery has been found to significantly reduce morbidity and post-operative recovery time.

However, percutaneous needle access of the surgical target may be difficult, and usually requires an extensive amount of experience and skill on the part of the surgeon. The above problem is exacerbated by the fact that prior art radiological image guidance techniques and associated imaging devices do not provide effective three dimensional information to the surgeon regarding needle insertion.

In order to overcome the above problem, several robotic systems have been proposed to date to assist in needle placement.

According to one solution, a stereopair of two x-ray views registered to a common fiducial system having an instrumented passive linkage with five degrees of freedom (or a "5DOF instrumented passive linkage") is used. The stereopair of views is used to position a passive needle guide. See Potamianos, P., Davies, B. L. and Hibberd, R. D., "IntraOperative Imaging Guidance for Keyhole Surgery Methodology and Calibration", Proceedings for the First International Symposium on Medical Robotics and Computer Assisted Surgery, Pittsburgh, Pa., pp. 98–104 (1994); see also Potamianos, P., Davies, B. L. and Hibberd, R. D., "Intra-Operative Imaging Guidance for Keyhole Surgery Methodology and Calibration", Proceedings for the First International Symposium on Medical Robotics and Computer Assisted Surgery, Baltimore, Md., pp. 156–164 (1995). It has further been proposed to provide an active needle guide in the form of an active robot instead of the passive needle guide mentioned above. See Bzostek, A., Schreiner, S., Barnes, A. C., Cadeddu, J. A., Roberts, W., Anderson, J. H., Taylor, R. H., Kavoussi, L. R., "An Automated system for Precise Percutaneous Access of the Renal Collecting System", submitted for review to the Proceedings of the First Joint conference of CVRMed and MRCAS, Grenoble, France (1997).

Although the above systems successfully address issues of image-to-robot registration and provide convenient means for defining target anatomy, they can nevertheless be expensive and cumbersome in an operating room environment. Moreover, for the implementation of the active robot mentioned above, the radiological profile of the end-effector, or needle, may interfere with a clear view of the target.

Percutaneous renal access procedures are often performed in radiology suites, where sophisticated imaging devices are available. Performing percutaneous surgery in the operative room has the advantage of significantly reducing cost, improving availability, and allowing the surgeon to have full control over the entire procedure. The imaging commonly available in the operating room involves uni-planar fluoroscopy provided by a "C-arm" imaging device, as described for example in U.S. Pat. No. 5,549,439.

Percutaneous surgery in the form of manual renal access normally proceeds according to a system of superimposed registration, which is described below.

The urologist positions a conventional C-arm imaging device over the renal collecting system, chooses the target calyx of the collecting system and the skin insertion site. The C-arm of the imaging device is then positioned, or "frogged", to register or align the desired skin insertion site and the target calyx so that they are superimposed in the image generated by the C-arm imaging device. The alignment of the desired skin insertion site and the target calyx defines the trajectory to be followed by the needle during its insertion, or the needle trajectory. Once the needle trajectory has been determined through a positioning of the C-arm, the C-arm is locked against changing its orientation, thereby resulting in an effective memorization of the needle trajectory. Next, the urologist manually holds the needle in position on the desired skin insertion site and in the direction of the needle trajectory memorized by the locked orientation of the C-arm. The needle, the insertion site and the target calyx are, as a result, superimposed as a single point on the image generated by the C-arm imaging device. Thereafter, the urologist manually inserts the needle into the insertion site while viewing the superimposed image to maintain the prescribed alignment along the needle trajectory.

A disadvantage of the above procedure is that it does not provide a simultaneous lateral view of the renal collecting system. The reason for the above is that the C-arm imaging device according to the mentioned procedure is used to maintain axial needle alignment, and can therefore not provide needle depth imagery. Therefore, according to the foregoing procedures, to gain access to the renal collecting system, the depth of insertion must be determined both as a function of the surgeon's experience and on a trial and error basis.

Additionally, the foregoing systems do not provide an effective needle driver which is both simple in its mechanical design and which exhibits a space-saving, miniaturized construction while allowing an efficient force and power transmission to the needle. Conventional needle driving techniques are based on holding the needle head and not the barrel of the needle, the motion of the needle being induced by moving the support of the needle head. The above technique does not allow radiolucent constructions. Moreover, supporting the needle from its head tends to disadvantageously maximize the unsupported length of the needle, thus facilitating needle deflection under the insertion force. Examples of such needle drive systems based on holding the needle head are included in the publication by Bzostek et al.

SUMMARY OF THE INVENTION

An object of the present invention is to provide a simple and effective method and system for radiological image guidance in percutaneous surgery which overcome the disadvantages of the prior art.

The above object, together with others to become apparent as the description progresses, is achieved by the provision of a method for performing radiological-image-guided percutaneous surgery with a system which includes a radiological image generating device for generating an image of a target anatomy of a patient to be operated on, and a needle insertion mechanism disposed adjacent the image generating device and having a needle adapted to be inserted into the patient. The method comprises the steps of: determining a needle trajectory of the needle by positioning the image generating device for aligning, in the image generated by the image generating device, a desired skin insertion site of the patient with a target region of the target anatomy; locking the needle in a direction of the needle trajectory; and repositioning the image generating device to obtain a lateral view of the needle trajectory for viewing an insertion depth and path of the needle during its insertion into the patient.

The invention further pertains to a system for performing the method described above, comprising: a radiological image generating device for generating an image of a target anatomy of a patient to be operated on for determining a needle trajectory to be followed through the patient, the image generating device being positionable to generate an image of the target anatomy from a plurality of directions; and a needle insertion mechanism disposed adjacent the image generating device and having a needle adapted to be inserted into the patient and to be locked in a direction of the needle trajectory.

According to one aspect of the invention, the needle insertion mechanism comprises both a needle and a needle driver, which includes: a first rotational component having a first contact face and being adapted to rotate about a rotational axis; and a second rotational component coaxial with the first rotational component and having a second contact face facing the first contact face and spaced therefrom, the needle being spaced from the rotational axis and further being pressed between the contact faces thereby applying an axial force to each of the contact faces directed parallel to the rotational axis, the axial force effecting a frictional engagement of the needle with the contact faces, the second rotational component further being adapted to rotate about the rotational axis such that, when the rotational components rotate about the rotational axis, the frictional engagement of the needle with the contact faces effects a translational motion of the needle.

The invention further pertains to a motion transmission mechanism comprising both an output shaft and an output shaft driver, which includes: a first rotational component having a first contact face and being adapted to rotate about a rotational axis; and a second rotational component coaxial with the first rotational component and having a second contact face facing the first contact face and spaced therefrom, the output shaft being spaced from the rotational axis and further being pressed between the contact faces thereby applying an axial force to each of the contact faces directed parallel to the rotational axis, the axial force effecting a frictional engagement of the output shaft with the contact faces, the second rotational component further being adapted to rotate about the rotational axis such that, when the rotational components rotate about the rotational axis, the frictional engagement of the output shaft with the contact faces effects a translational motion of the output shaft.

The simplicity of the method and system according to the present invention is achieved by combining the proven radiological image guidance procedures and devices of the prior art with a simple and cost-effective needle injection device which exhibits an extremely low radiological profile. The needle injection device further provides actuated needle motion in conjunction with a mechanical manipulator designed to be used in existing operating rooms without the necessity of additional computers or personnel.

Accordingly, the method and device of the present invention mimic and improve upon the surgeon's standard technique. The key advantages of the present invention are that it involves the use of a proven radiological needle alignment procedure, improves accuracy in comparison with purely manual needle positioning techniques, and enables lateral fluoroscopic monitoring of the needle without necessitating computer-based vision and robotic systems. The present invention results in a shortening of procedure durations, improves upon patient safety, ensures and improves upon equipment sterility, and reduces the radiation exposure of surgeons.

According to the present invention, a method and system are provided which, to an extent, mimic the surgical technique of superimposed registration used in the prior art and described above. Thus, the invention contemplates registering or aligning a C-arm and needle according to the prior art. However, in the accordance with the invention, the needle is mechanically locked so as to lock the needle axis along the desired needle trajectory by any suitable means, and preferably by a robotic manipulator. Thus, the needle trajectory according to the invention is memorized by a locked orientation of the needle proper, and not of the C-arm, thereby allowing the surgeon to position or "frog" the C-arm to obtain a lateral view of the target anatomy and needle. As a result, the insertion depth of the needle and the path of the needle during its insertion may be observed directly by the surgeon on the image provided by the laterally positioned C-arm. Direct observation of insertion depth advantageously allows the surgeon to compensate for soft tissue deflection of the target, such as the kidney, surrounding tissue. Thus, in comparison with prior art techniques, the method according to the present invention results in safer and more accurate percutaneous procedures.

A further advantage of the method according to the invention is that it does not require image correction and calibration. By superimposing the needle, the insertion site and the target, any image distortions are identical, and therefore, cancel each other. Moreover, the method of the present invention requires direct observation by only the surgeon involved, and hence does not necessitate image-processing that is computer based, thereby significantly reducing operative time and expense.

In order to drive the needle according to the present invention, a needle driver is provided which converts rotational to translational motion in a transmission element which is adapted to receive the barrel of the needle therein. Power is transmitted to the needle through friction forces from contact faces between which the needle is pressed. Thus, the novelty of the transmission resides in providing a mechanism in which a force is generated which extends in the direction of the axis of rotation and which is normal to the direction of friction forces thus leading to the conversion of the rotational motion to the translational motion mentioned above. The needle driver constructed according to the invention thus results in axial loading of the contact faces which is significantly larger than similarly sized radial loading systems of the prior art, yielding increased efficiency in the transmission of force and power. While mechanisms involving the conversion of rotational motion to translational motion through friction abound in the prior art, these systems involve the generation of a force which is oriented only radially with respect to the axis of rotation, and not axially with respect to this axis. On the other hand, the invention advantageously involves an axially loaded friction mechanism for converting rotational motion to translational motion.

Additionally, the needle driver according to the invention, by virtue of providing a construction where the needle is held by its barrel and not by its head, allows a radiolucent construction and advantageously decreases the unsupported length of the needle for substantially preventing needle deflection under the insertion force.

BRIEF DESCRIPTION OF THE DRAWINGS

The foregoing objects of the invention, together with other objects and advantages which may be attained by its use, will become more apparent upon a review of the following detailed description of the invention taken in conjunction with the drawings. In the drawings, where like reference numerals identify corresponding components:

FIG. 5b is a detail of the view shown in FIG. 5a;

FIG. 7b is a schematic cross-sectional view taken along line 7b—7b in FIG. 7a;

DETAILED DESCRIPTION OF THE INVENTION

Figure 1:
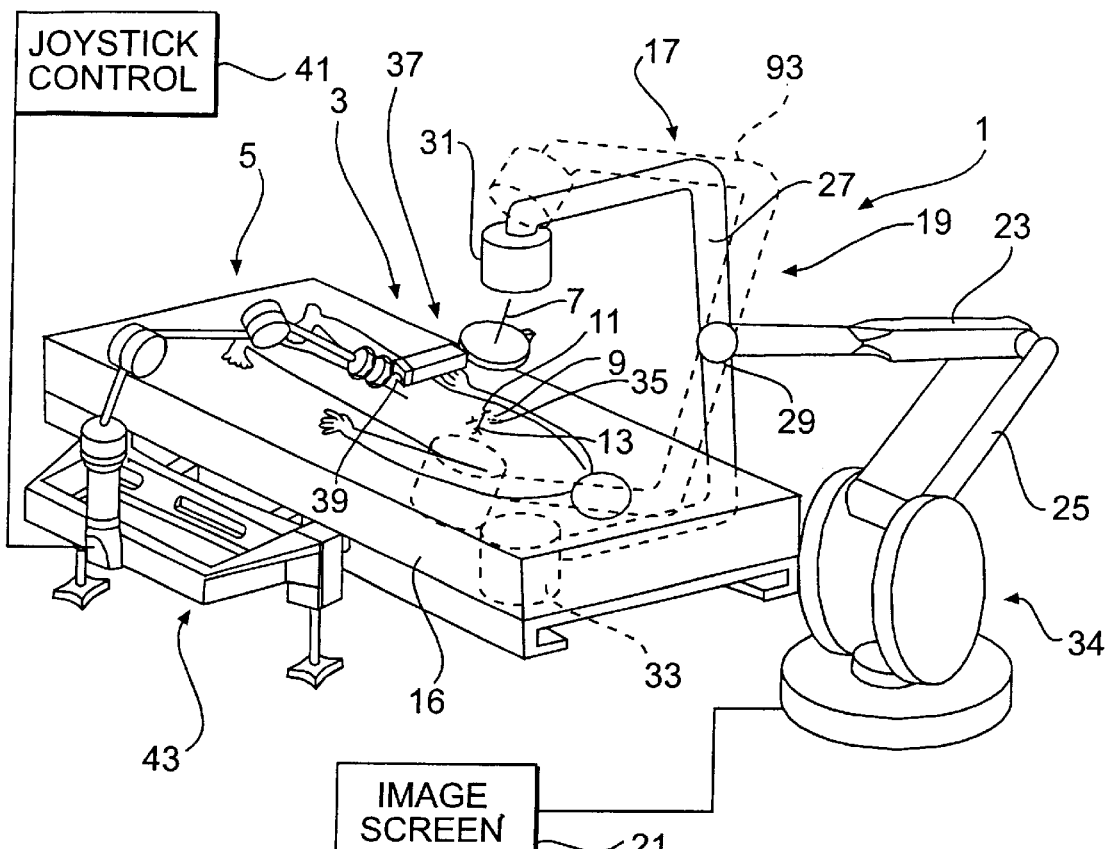
FIG. 1 is a perspective view of a system for radiological image guidance in percutaneous surgery.

As seen in FIG. 1, a system 1 for radiological image guidance in percutaneous surgery is shown. The system is disposed in an area suitable for surgery, such as an operating room. A novel needle insertion mechanism 3 comprises a passive needle manipulator 5 which maintains the needle 7 in position above a patient 9, and is effective in minimizing the surgeon's radiation exposure and disturbances in the needle trajectory during the insertion of the needle through insertion site 11 toward target 13. System 1 requires neither a fully actuated robot nor position feedback sensors by virtue of using a superimposed registration technique as described previously, thus minimizing costs.

As further shown in FIG. 1, the system further includes an operating room table 16 for the patient, and a conventional C-arm imaging device 17 including a C-arm 19 and an image screen 21. The C-arm imaging device may, for example, comprise the X-ray system disclosed in U.S. Pat. No. 5,549,439. Thus, by way of example, C-arm 19 comprises a top arm 23 hingedly connected to a bottom arm 25 and pivotable by means of a suitable actuator 34 about a horizontal axis. A C-shaped bracket 27 is fixed to the free end 29 of top arm 23. The C-arm. imaging device 17 further comprises an X-ray radiation source 31 at a free end thereof. The other free end of bracket 10 bears an X-ray image sensor 33 which lies in the radiation beam of source 31. As can be seen from FIG. 1, bracket 27 is suspended from free end or wrist 29 so that it can be pivoted about three axes which are at right angles to one another. An X-ray image generated by the C-arm imaging device 17 can be seen on screen 21 coupled to the source 31 and sensor 33.

Figure 2:
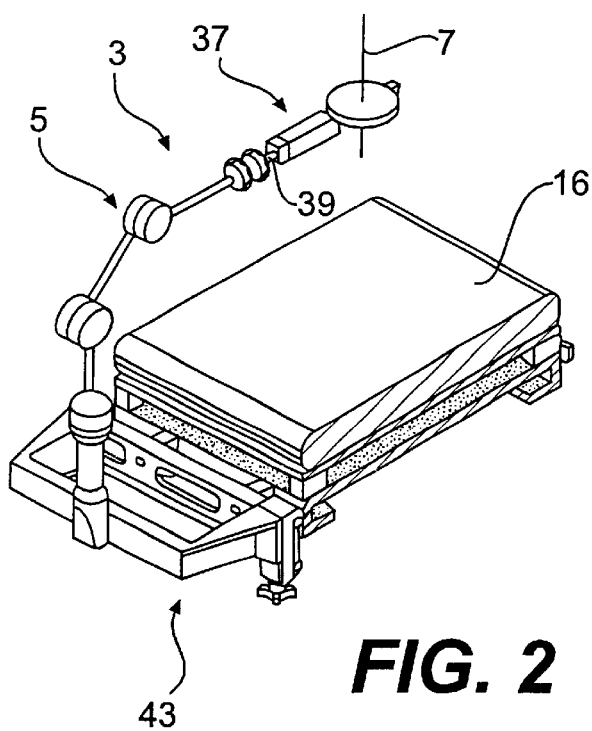
FIG. 2 is a perspective view of the manipulator of the system according to FIG. 1 attached to an operating table shown in a partially sectional view.

Manipulator 5 shown in FIGS. 1 and 2 is preferably an FDA approved manipulator arm sold under the trademark LEONARD and manufactured by Leonard Medical, Inc. Manipulator 5 has six degrees of freedom made possible by the provision of three rotational joints and one spherical joint. The joints may be spring loaded (not shown) to compensate for gravitational loading, and are not equipped with motors or position encoders. These joints may be locked in the desired position, preferably simultaneously, as dictated, for example, by a needle trajectory 35 determined through the superimposed registration technique described above. A locking of the joints may be effected, for example, by vacuum operated brakes (not shown).

The needle insertion mechanism 3 shown in FIGS. 1 and 2 further comprises an active needle driver 37 attached to the distal end of passive arm 39 of the manipulator 5. Needle driver 37 is shown in FIG. 1 as being disposed between source 31 and sensor 33 such that the axis of the needle can be aligned along the X-ray. Needle driver 37 may be actuated by a variable speed DC motor which the surgeon regulates via a conventional joystick control 41. As disclosed in U.S. Pat. No. 5,116,180, joystick technology for effecting manipulations in multiple degrees of freedom is well within the skill of the artisan.

As further seen in FIGS. 1 and 2, a custom designed rigid side rail 43 is mounted on table 16 to provide a sturdy base for the manipulator 5. The provision of a rigid side rail is critical for maintaining the needle trajectory under the insertion force of the needle.

Needle driver 37 is preferably constructed of plastic, such as acrylic, and could be manufactured inexpensively as a disposable unit. Needle driver 37 is easily sterilized and is further made of a material and/or materials which are almost completely radiolucent, thus enabling the surgeon to monitor the surgery with an unimpeded fluoroscopic image.

Figure 3:
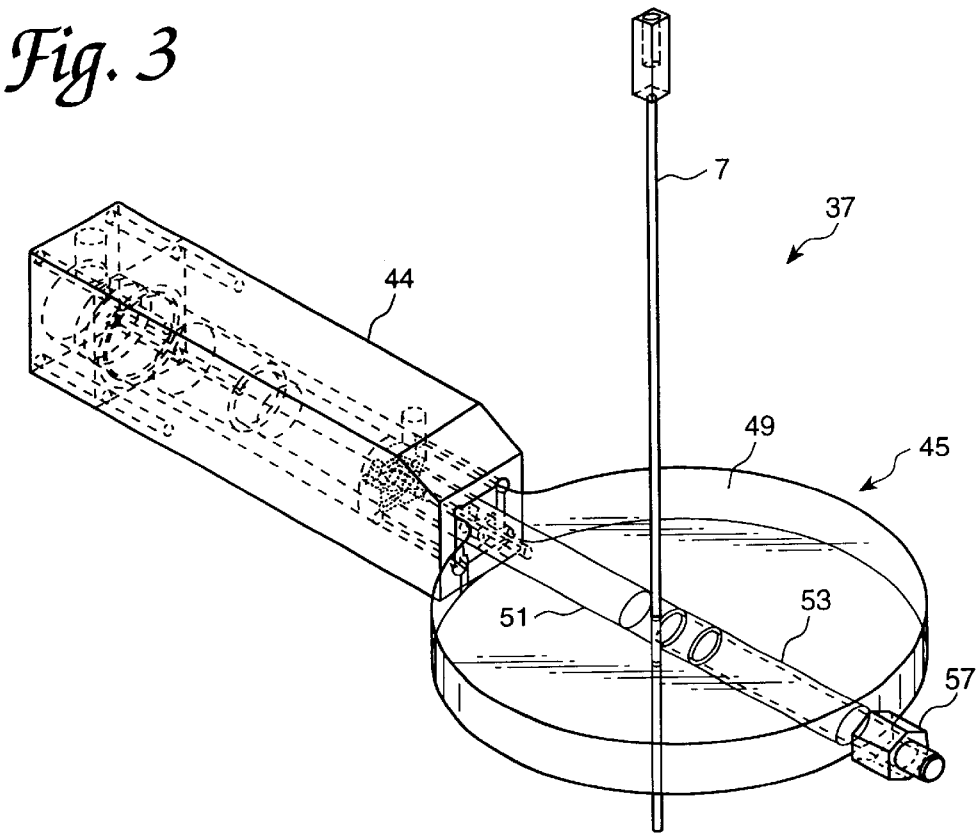
FIG. 3 is a perspective view of a needle driver of the manipulator of FIG. 2.

A novel feature of the insertion device is that it grasps the barrel of the needle and not the head of the needle, as seen in FIGS. 1–3, and as described in further detail below. The above significantly reduces the unsupported length of the needle during insertion, thus advantageously minimizing lateral flexure thereof under insertion loading.

As seen in FIG. 3, needle driver 37 comprises a needle driver housing 44, and a transmission element 45 mounted on the housing, preferably by means of a ball lock mechanism (not shown). The transmission element comprises a trocar needle 7 used as the output shaft thereof. An input shaft 47 of transmission element 45 is driven by a DC motor (not shown), which is located in part in needle driver housing 44.

Figure 4:
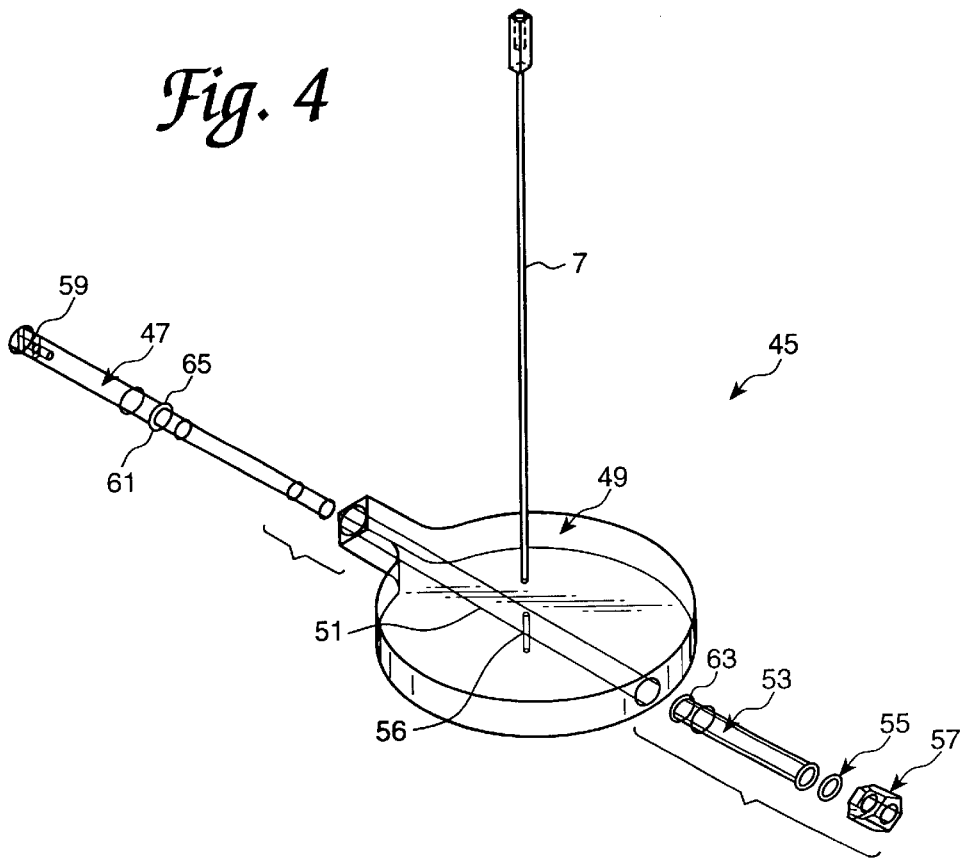
FIG. 4 is an exploded view of the transmission element of the needle driver of FIG. 3.

FIG. 4 shown an exploded view of transmission element 45 which comprises a transmission housing 49 preferably constructed of acrylic or other radiolucent material. Transmission housing 49 defines a first rimmed bore 51 extending thereacross and adapted to slidingly receive input shaft 47 and an axial-loading bushing 53 therein. Bushing 53 slides over input shaft 47, best seen in FIG. 4, and is axially loaded through O-ring 55 with a nut 57. Transmission housing 49 further defines a second rimmed bore 56 therein transversely tangential to first rimmed bore 51 within transmission housing 49 as shown. Input shaft 47, bushing 53 and nut 57 are likewise preferably constructed of acrylic or other radiolucent material. Input shaft 47 is further coupled at a driven end 59 thereof to the D.C. motor, and at another end thereof to nut 57. By coupling input shaft 47 to nut 57, the D.C. motor drives bushing 53 indirectly through nut 57 at the same rotational speed as input shaft 47. Bushing 53 is driven by loading O-ring 55 with nut 57. In the shown construction, the O-ring has a function equivalent to that of a spiral spring, and is used instead of the spring in order to achieve better radiolucency.

The disc-shaped construction of transmission housing 49 advantageously provides a large surface around needle 7 which presents a uniform thickness and density for exhibiting a uniform attenuation of the X-ray image such that views of the target and biological surfaces surrounding the same are not impeded during percutaneous surgery.

Figure 5A:
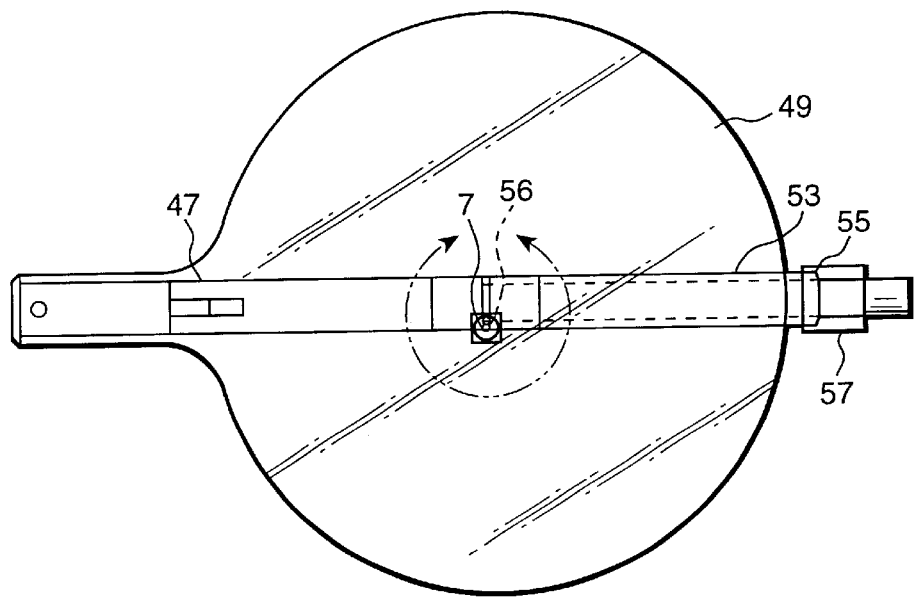
FIG. 5a is a top plan view of the transmission element of FIG. 4.
Figure 5B:
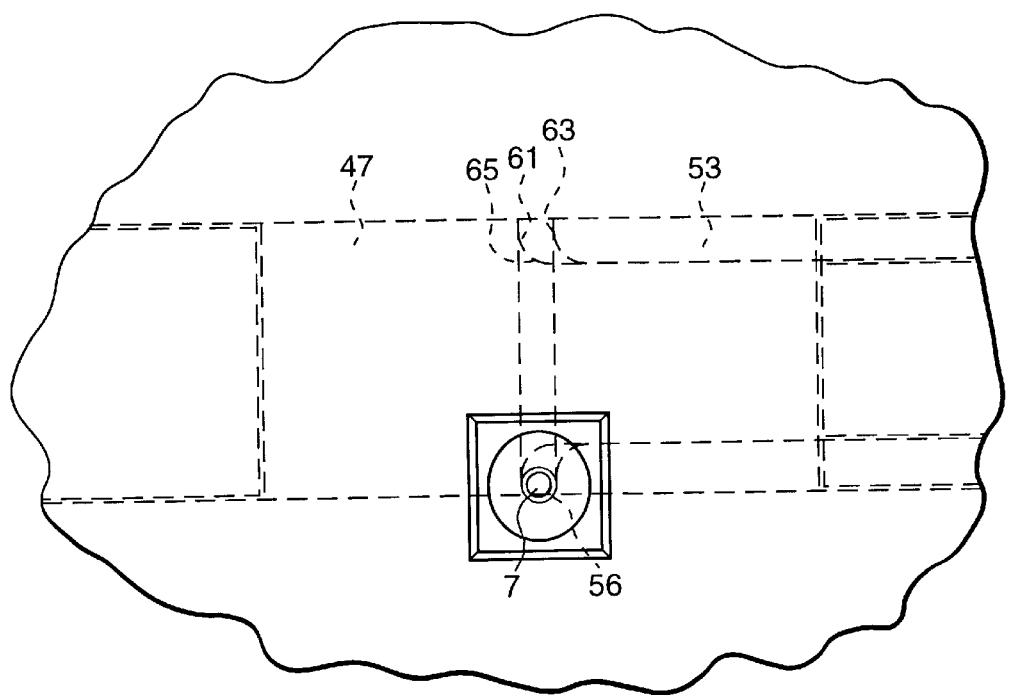

FIG. 5a is a top view of the assembly, while FIG. 5b shows a detail of FIG. 5a. As shown in FIGS. 5a and 5b, needle 7 slides in the second rimmed bore 56 of transmission housing 49, and is, as a result, pressed between a contact face 61 of input shaft 47 and contact face 63 of bushing 53, which contact face 63 corresponds to one of the two ends of the bushing. Contact faces 61 and 63 impart an axial force to needle 7 corresponding to the transmission friction force between the contact faces and needle 7. A fillet 65 may be placed at the base of contact face 61 of the input shaft 47 to diminish a high concentration of stress at that location, which corresponds to the weak point of the shaft.

The transmission between the contact faces 61 and 63 tends to slip when overloaded. The overload force, however, is adjustable through a manipulation of nut 57.

The above design of needle driver 37 allowed, during one test, the generation of a drive force of up to 30 Newtons for a maximum pre-load. The needle was placed as close as possible to contact face 61 of input shaft 47. The above arrangement resulted in an efficiency of approximately 85% of the transmission.

Figure 9:
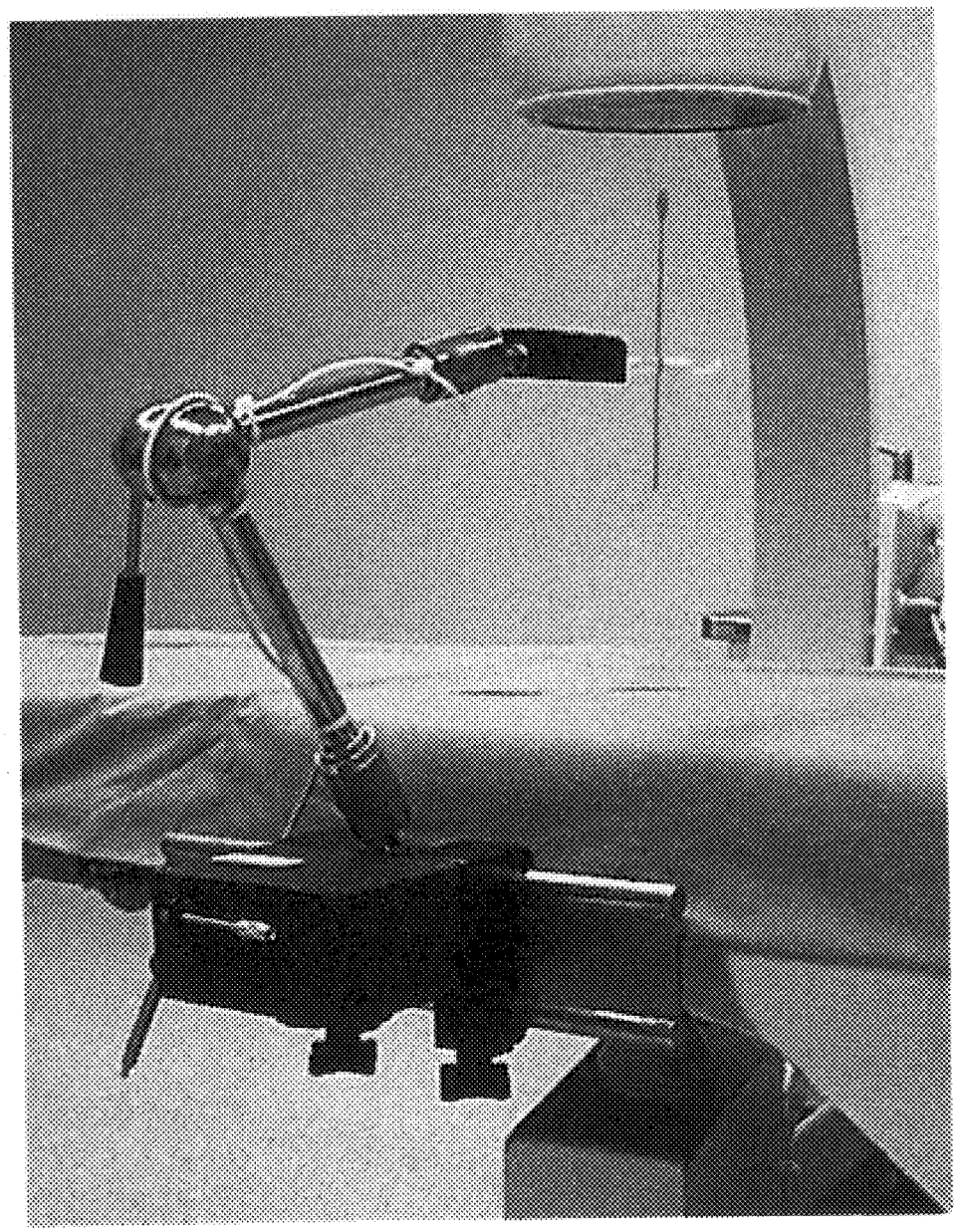
FIG. 9 is a photograph of an exemplary system for radiological image guidance in percutaneous surgery, in accordance with the invention.

A photograph of an exemplary system for radiological image guidance in percutaneous surgery in accordance with the invention shown in FIG. 9.

Figure 6:
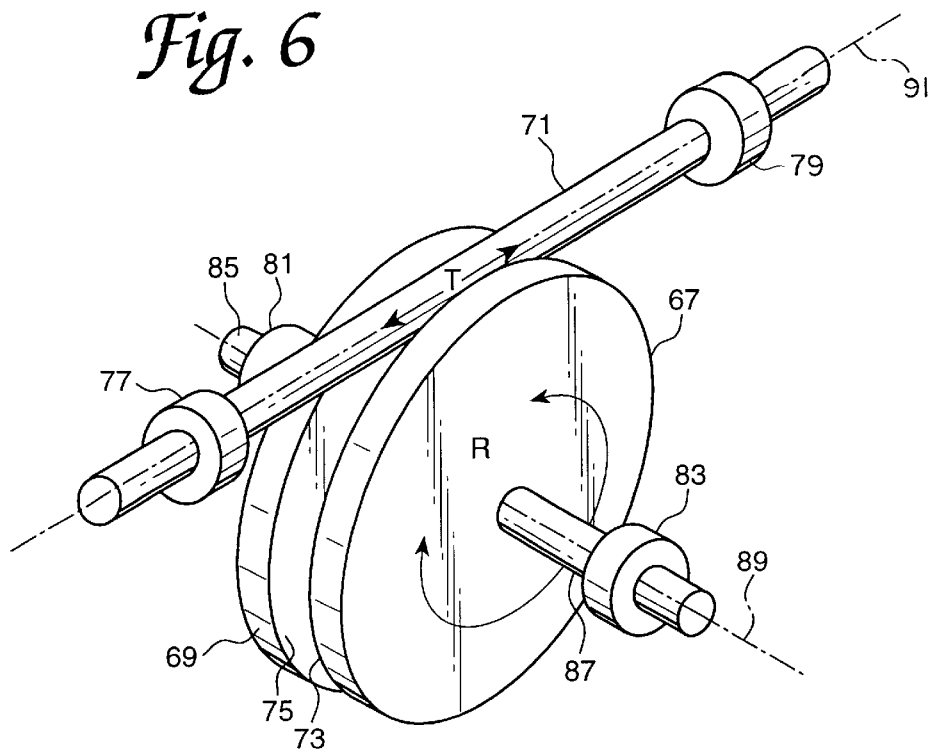
FIG. 6 is a perspective schematic view of an axially loaded friction transmission mechanism which functions according to the same principle as the needle driver of the present invention.
Figure 7A:
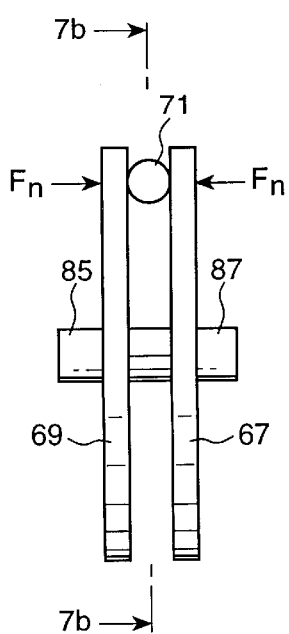
FIG. 7a is a schematic front view of the mechanism of FIG. 6.
Figure 7B:
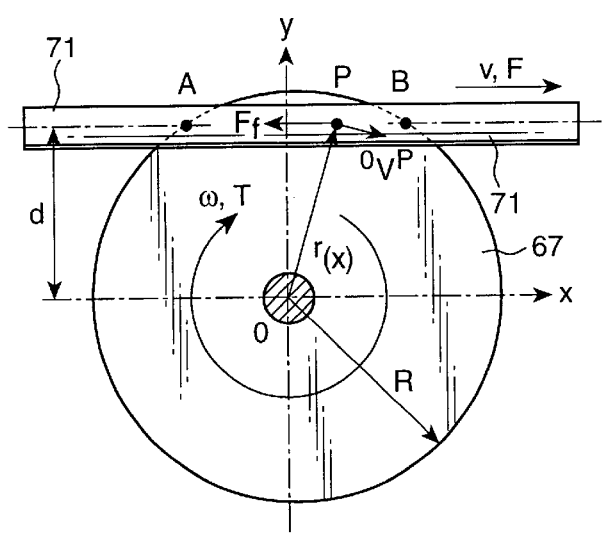

FIGS. 6, 7a and 7b provide a more detailed understanding of the principle involved in the operation of the needle drive according to the present invention by providing illustrations of a mechanism which functions similarly to the needle drive. Thus, as shown in FIGS. 6, 7a and 7b, the non-backlash transmission mechanism converts the rotational motion indicated by arrow R of disks 67 and 69 into a translational motion indicated by arrow T, and vice versa. Output shaft 71 is squeezed between contact faces 73 and 75 of disks 67 and 69 which generate the transmission friction. As seen in FIG. 6, bushings 77, 79, 81 and 83 are fixed against movement for maintaining the relative position of the shafts. The kinematics of the shown mechanism is shown more clearly in FIGS. 7a and 7b.

As seen in FIGS. 7a and 7b, disks 67 and 69 are axially loaded with the force $F_f = \mu F_n$. Here, $\mu$ is the Coulomb coefficient of friction between disks 67 and 69 and the output shaft 17. The output force of the transmission, that is, F, is bounded by $2F_f$, which means that $F \leq 2F_f$. Therefore, the transmission slips when overloaded, as mentioned with respect to the needle driver above. Theoretically, the friction force acts on contact line AB on contact faces 73 and 75 of disks 67 and 69, respectively. In a planar Newtonian system of coordinates xOy as shown in FIG. 7b centered on the rotational axis 89 of inputs shafts 85 and 87, the absolute velocity of a contact point P on either of the disks 67 or 69 with respect to point O is given by the equation:

$$^{O}V^{P} = \omega r_{(x)} \qquad \text{(eq. 1)}$$

where $\omega$ is the angular velocity of inputs shafts 85 and 87 and $r_{(x)}$ is the position vector of point P. The x and y components of V may be calculated according to the following equations:

$$^{O}V^{P}_{x} = \omega d \qquad \text{(eq. 2a)}$$

$$^{O}V^{P}_{y} = -\omega x \qquad \text{(eq. 2b)}$$

where d is the distance between the input shaft rotational axis 89 and the output shaft axis 91, and coordinate x defines the position of point P on line AB. From the equations above, it can be seen that $^{O}V^{P}_{x}$ is constant along line AB and $^{O}V^{P}_{y}$ is linearly dependent on x. The first equation defines the kinematic transfer function of the transmission as:

$$V = \omega d \qquad \text{(eq. 2c)}$$

where V is the translational velocity of output shaft 71 and is the angular velocity of inputs shafts 85 and 87. Similarly, the dynamic transfer function of the transmission may be calculated as:

$$F = T/d; \quad F \leq 2\mu F_n \qquad \text{(eq. 3)}$$

where T is the input torque.

The transmission of rotational motion to translational motion and vice versa dissipates mechanical power due to the y-directional sliding friction of disks 67 and 69 with respect to output shaft 71 on contact line AB. The velocity of a point P of either one of the disks relative to output shaft 71 (when the transmission is under-loaded, (that is, when $F \leq 2 \mu F_n$) is given by:

$$^{71}V^{P}_{x} = 0 \qquad \text{(eq. 4a)}$$

$$^{71}V^{P}_{x} = -\omega x \qquad \text{(eq. 4b)}$$

The above equations show that there is no energy loss due to the x-directional friction. However, the y-directional friction components exhibit energy dissipation and hence mechanical work. The lost energy $W_l$ and transmitted energy $W_t$ of the transmission may be calculated using the Coulomb friction model according to the following equations:

$$W_l = (4/21)_0 \int^l F_f \, ^{71}V^{P}_y \, dx = -\mu F_n \omega 1 \qquad \text{(eq. 5a)}$$

$$W_t = 2F_f \, ^{71}V^{P}_y = 2\mu F_n \omega d \qquad \text{(eq. 5b)}$$

where $$l = (|AB|/2) = \sqrt{R^2 - d^2}$$

where R is the radius of disks 67 and 69. In arriving at equations 5a and 5b, maximum loading $F = 2 \mu F_n$ of the transmission was considered, and the static and dynamic coefficients of friction p were considered equal (which amounts to the most disadvantageous case). As a result of the above, the power efficiency of the transmission may be calculated as:

$$\epsilon_{(d)} = W_t / (W_t - W_l) = 2d/(2d + 1) \qquad \text{(eq. 6)}$$

noting that the efficiency depends solely on the ratio of d in R. Defining the above ration as $f = d/R$, the efficiency of the transmission becomes:

$$\epsilon_{(d)} = 2f/(2f + \sqrt{1 - f^2}) \qquad \text{(eq. 7)}$$

Figure 8:
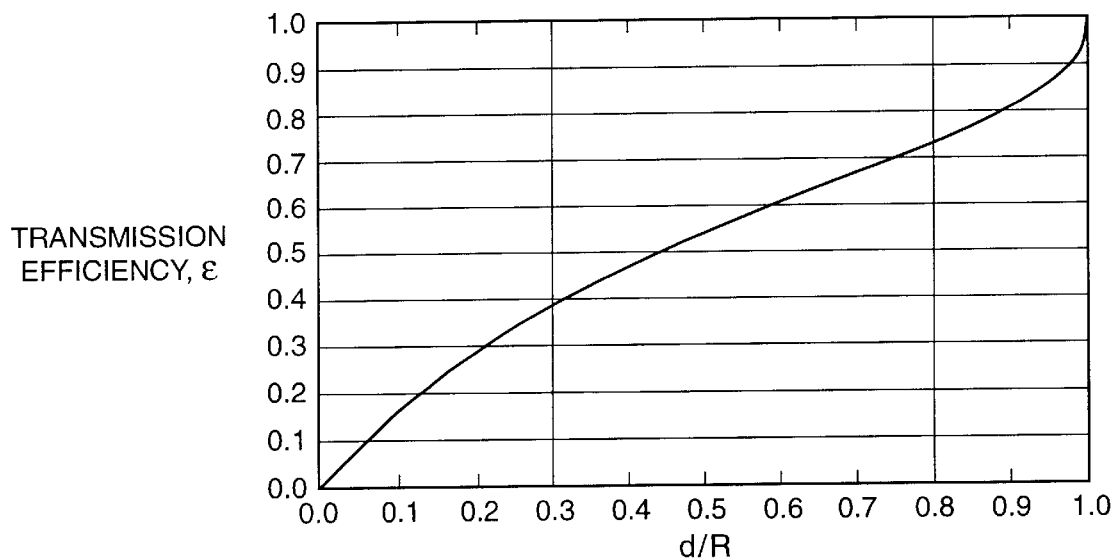
FIG. 8 is a graph of the dependence of the transmission efficiency on the position of the output shaft with respect to the input shafts of the mechanism shown in FIGS. 6, 7a and 7b.

The dependence of the efficiency on the position of the output shaft 71 with respect to the input shafts 85 and 87 is graphically represented in FIG. 8. The extremes of the graph shown in FIG. 8 illustrate the output power is 0 if d=0 and no power is lost if d=R. Thus, the graph suggests that the dimension d should be set as close to R as possible in order the maximize the efficiency of the transmission.

It is noted that in the mechanism shown in FIGS. 6, 7a and 7b, a rotational motion may be imposed over the translational motion of output shaft 71 by either using different materials (which lead to different coefficients of friction) for the respective disks 67 and 69, or by slightly inclining the axis 91 of the output shaft 71 with respect to the rotational axis 89 of the disks 67 and 69 in the y direction.

It can be appreciated from the mechanism depicted in FIGS. 6, 7a and 7b that the mechanism functions according to the principle described for the needle driver 37 of the present invention. Thus, input shafts 85 and 87 in FIGS. 6, 7a and 7b correspond, respectively, to input shaft 47 and bushing 53 shown in FIGS. 3, 4, 5a and 5b, since input shafts 85 and 87 transmit rotational motion. Moreover, contact faces 73 and 75 of disks 67 and 69 in FIGS. 6, 7a and 7b correspond to contact faces 61 and 63 of input shaft 47 and bushing 53 in FIGS. 3, 4, 5a and 5b, while output shaft 71 in FIGS. 6, 7a and 7b corresponds to needle 7 shown in FIGS. 1–4, 5a and 5b. Moreover, by being fixed against movement for maintaining the relative position of the shafts, bushings 77 and 79 on the one hand, and 81 and 83 on the other hand, as shown in FIG. 6, correspond to ends of second rimmed bore 56 and to ends of first rimmed bore 51 shown in FIGS. 3, 4, 5a and 5b, respectively.

The above description of the principle of operation of the needle driver 37 makes it clear that greater transmission efficiency may be obtained by placing the needle 7 closer to radial edges of contact faces 61 and 63 of input shaft 47 and 5 bushing 53, as suggested by the graph of FIG. 8.

As an example of the method according to the present invention, a percutaneous procedure involving renal access is described below.

According to the present invention, the urologist positions C-arm imaging device 17 over the renal collecting system of patient 9, chooses the target calyx 13 and the skin insertion site 11. The C-arm is then positioned to align the desired skin insertion site and the target calyx so that they are superimposed in the image generated by the C-arm. The alignment of the desired skin insertion site and the target calyx defines the trajectory to be followed by the needle during its insertion, or the needle trajectory 35. Once the needle trajectory has been determined through a positioning of the C-arm, the needle 7 is mechanically locked so as to lock the needle axis along the desired needle trajectory 35 by locking manipulator 5 to hold the needle in the desired orientation. Thus, the needle trajectory according to the invention is memorized by a locked orientation of the needle proper, and not of the C-arm, thereby allowing the surgeon to position or "frog" the C-arm to obtain a lateral view of the target anatomy and needle. As a result, the insertion depth of the needle and the path of the needle during its insertion may be observed directly by the surgeon on the image provided by the laterally positioned C-arm, indicated by broken lines 93 in FIG. 1. Direct observation of insertion depth advantageously allows the surgeon to compensate for soft tissue deflection of the target, such as the kidney, and surrounding tissue.

The invention addresses a particularly difficult surgical task by designing a simple and cost-effective robotic system and method which can be rapidly transferred to the clinical setting. One of the important advantages of the method and system according to the invention is the uncomplicated mimicry they provide of the surgeon's technique while improving both the safety and the accuracy of percutaneous procedures. The invention is fully compatible with, but does not require a computer-based vision system or a fully actuated robot with joint position feedback.

The full content of all of the documents and/or patents mentioned in this specification is incorporated herein by reference.

Although only the preferred embodiments have been described in detail above, those of skill in the art will readily appreciate that many modifications of the exemplary embodiments are possible without departing from the spirit or scope of the invention as set forth in the appended claims.

What is claimed is:

1. A method for performing radiological-image-guided percutaneous surgery with a system which includes a radiological image generating device for generating an image of a target anatomy of a patient to be operated on, and a needle insertion mechanism having a needle adapted to be inserted into the patient, the method comprising:

determining a needle trajectory of the needle by positioning the image generating device for aligning a desired skin insertion site on the patient with a target region of the target anatomy in an image generated by the image generating device;

locking the needle along the needle trajectory, the locking being performed by pressing the needle between first and second contact faces of rotational components provided in the needle insertion mechanism such that an axial force directed parallel to a rotational axis of the rotational components effects frictional engagement between the contact faces and the needle, and such that as the rotational components rotate about the rotational axis, the frictional engagement effects a translational motion of the needle; and repositioning the image generating device to obtain a lateral view of the needle trajectory for viewing an insertion depth and path of the needle during insertion thereof into the patient.

2. The method for performing radiological-image-guided percutaneous surgery according to claim 1, wherein the locking is carried out by the needle insertion mechanism and at least portions of the needle insertion mechanism comprise radiolucent material so as to permit x-rays to pass through the needle insertion mechanism and permit a substantially unobstructed fluoroscopic image.

3. A system for performing radiological-image-guided percutaneous surgery, comprising:

a radiological image generating device for generating an image of a target anatomy of a patent to be operated on, the image generating device being positionable to generate an image of the target anatomy from a plurality of directions, whereby, in the image generated by the image generating device, a desired skin insertion site can be aligned with a target region of the target anatomy, to determine a needle trajectory to be followed through the patient; and a needle insertion mechanism disposed adjacent the image generating device and having a needle adapted to be inserted into the patient, said needle insertion mechanism comprising radiolucent material so as to allow x-rays to pass therethrough and permit a substantially unobstructed fluoroscopic image, and being constructed and arranged to lock the needle in a direction of the needle trajectory determined with said radiological image generating device.

4. The system according to claim 3, wherein the needle insertion mechanism comprises:

a first rotational component defining a first contact face and being constructed and arranged to rotate about a rotational axis; and a second rotational component coaxial with the first rotational component and defining a second contact face facing the first contact face and spaced therefrom, the needle being spaced from the rotational axis and further being pressed between the contact faces thereby applying an axial force to each of the contact faces directed parallel to the rotational axis, the axial force effecting a frictional engagement of the needle with the contact faces, the second rotational component further being rotatable about the rotational axis such that, when the rotational components rotate about the rotational axis, the friction engagement of the needle with the contact faces effects a translation motion of the needle.

* * * * *